United States Patent [19]
Murtha

[11] 4,115,206
[45] Sep. 19, 1978

[54] SEPARATION OF PHENOL-, CYCLOHEXANONE-, AND CYCLOHEXYLBENZENE-CONTAINING MIXTURES EMPLOYING AN ORGANIC CARBONATE

[75] Inventor: Timothy P. Murtha, Bartlesville, Okla.

[73] Assignee: Phillips Petroleum Company, Bartlesville, Okla.

[21] Appl. No.: 817,883

[22] Filed: Jul. 21, 1977

[51] Int. Cl.$^2$ .................. B01D 3/40; C07C 39/04; C07C 45/24
[52] U.S. Cl. ........................................ 203/60; 203/84; 260/586 R; 568/749
[58] Field of Search .................. 203/60, 51, 62, 58, 203/57, 38, 84; 260/586 R, 586 P, 621 A, 621 C

[56] References Cited

U.S. PATENT DOCUMENTS

| | | | |
|---|---|---|---|
| 2,762,760 | 9/1956 | Walker | 260/621 A |
| 3,018,228 | 1/1962 | Cornell | 203/58 |
| 3,227,632 | 1/1966 | Schmalenbach et al. | 203/58 |
| 3,554,873 | 1/1971 | Luther et al. | 203/60 |
| 4,016,049 | 4/1977 | Fozzard et al. | 203/60 |
| 4,019,965 | 4/1977 | Fozzard | 203/60 |
| 4,021,490 | 5/1977 | Hudson | 260/621 C |

Primary Examiner—Wilbur L. Bascomb, Jr.

[57] ABSTRACT

Phenol-, cyclohexanone-, and cyclohexylbenzene-containing mixtures are extractively distilled employing an organic carbonate to provide overhead of high purity cyclohexanone and a kettle product substantially free of cyclohexanone and containing phenol, the organic carbonate, and, when present in the mixture, cyclohexylbenzene.

4 Claims, 1 Drawing Figure

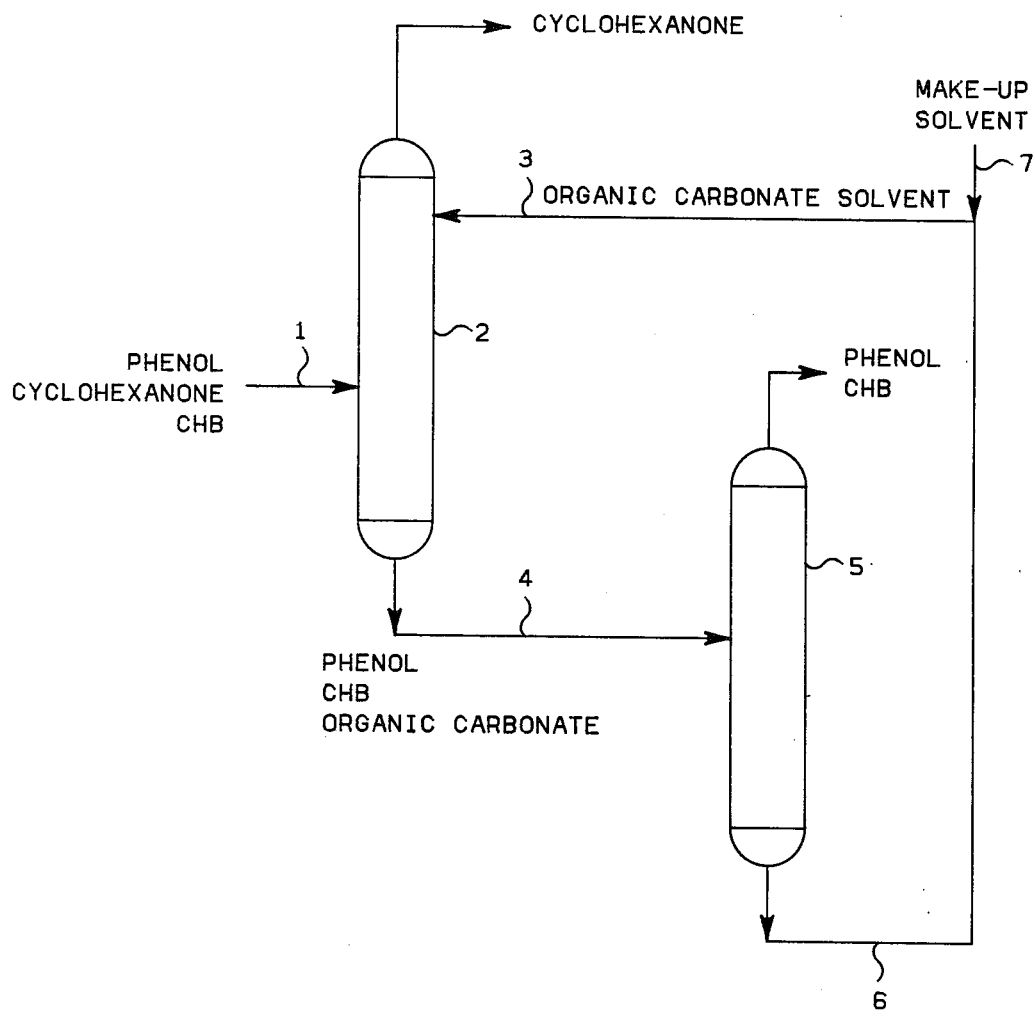

SEPARATION OF PHENOL-, CYCLOHEXANONE-, AND CYCLOHEXYLBENZENE-CONTAINING MIXTURES EMPLOYING AN ORGANIC CARBONATE

This invention relates to separation of phenol from its azeotropes, including phenol-cyclohexanone azeotropes, which may be in presence of cyclohexylbenzene. In one of its aspects, the invention relates to the recovery of phenol and cyclohexanone from the cleavage products resulting from cleavage of the oxidation product of cyclohexylbenzene to provide a cyclohexylbenzene hydroperoxide which then is converted to produce the phenol, cyclohexanone, and any unreacted cyclohexylbenzene.

In one of its concepts, the invention provides a process for the extractive distillation of a mixture containing phenol and cyclohexanone employing as an agent an organic carbonate. In another of its concepts, the invention provides for the recovery of cyclohexanone from mixtures resulting from cleavage of the oxidation product of cyclohexylbenzene to provide cyclohexylbenzene hydroperoxide.

In a further concept of the invention, the extractive distillation yields an overhead product containing essentially only cyclohexanone. The extract will contain phenol, a small quantity of cyclohexanone, cyclohexylbenzene when it is present in the mixture to be separated, and the organic carbonate. The extract is further separated by stripping and fractionation or otherwise to recover phenol and cyclohexylbenzene therefrom whereupon the organic carbonate can be reused as solvent in the extractive distillation.

It is an object of this invention to separate mixtures containing phenol and cyclohexanone which mixtures also can contain cyclohexylbenzene. It is another object of this invention to provide an extractive distillation agent or solvent to separate mixtures as herein described. It is a still further object of the invention to provide an extractive distillation operation comprising a mixture containing one or more agents or solvents, also as described herein.

Other aspects, concepts, objects, and the several advantages of the invention are apparent from a study of this disclosure and the appended claims.

According to the present invention, a mixture containing phenol and cyclohexanone, which may also contain cyclohexylbenzene, is extractively distilled and thus separated to produce as an overhead product a fraction consisting essentially of cyclohexanone of high purity employing an organic carbonate.

Cyclohexylbenzene (CHB) can be converted to phenol and cyclohexanone via cyclohexylbenzene hydroperoxide. The acid catalyzed cleavage of cyclohexylbenzene hydroperoxide in the presence of unoxidized CHB results in a mixture of CHB, phenol, and cyclohexanone. This mixture is difficult to separate by conventional distillation techniques because phenol and cyclohexanone form an azeotrope (b.p. 184° C at atmospheric pressure) containing about 72 weight percent phenol. In addition, CHB codistills with this azeotrope.

Mixture to be Separated

Any mixture of phenol, cyclohexanone, and CHB or phenol and cyclohexanone can be used. It is within the scope of this invention to remove by suitable methods a portion of any of the components from the mixture to be separated prior to the extractive distillation with organic carbonates. For example, any excess of cyclohexanone over the quantity present in the azeotrope can be first distilled from the mixture as an essentially pure material. Since CHB codistills with the phenol/cyclohexanone azeotrope in quantities of about 2 to 10 weight percent, any excess of CHB over that amount can be removed by fractional distillation to take the phenol/cyclohexanone mixture containing about 2 to 10 weight percent CHB overhead. It is also within the scope of this invention to remove essentially all of the CHB from the mixture by suitable techniques, such as extractive distillation, prior to the extractive distillation of this invention.

Solvent

The organic carbonate solvent to be used in the extractive distillation of this invention can contain up to 30 carbon atoms and can be represented by general formula I:

wherein R and R' are each selected from a group consisting of alkyl radicals containing 4 to 18 carbon atoms, cycloalkyl radicals containing 5 to 12 carbon atoms, aryl or substituted aryl radicals containing 6 to 12 carbon atoms with the substituent groups being one or more or a mixture of alkyl, alkoxy, cycloalkyl, halogen, or the like, and aralkyl radicals containing 7 to 12 carbon atoms, or wherein R and R' taken together form a ring represented by Formula II:

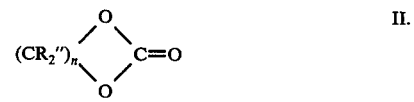

wherein $n$ is 2 or 3 and each R" is selected from the group consisting of hydrogen, alkyl radicals containing 1 to 4 carbon atoms, aryl or substituted aryl radicals containing 6 to 12 carbon atoms with the substituent groups being alkyl, alkoxy, cycloalkyl, halogen, or the like and aralkyl radicals containing 7 to 12 carbon atoms and the organic carbonate solvent selected has a boiling point above the boiling point of phenol (182° C at atmospheric pressure) to facilitate the separation of phenol and solvent by fractional distillation.

Low levels of phenol (up to about 10 weight percent phenol) can be present in the recovered and recycled solvent with no detrimental effect on the extractive distillation. For ease of handling, it is preferred that the organic carbonate used as an extractive distillation solvent be a liquid or low melting (below about 80° C) solid.

Specific examples of suitable organic carbonate solvents include dioctyl carbonate, diphenyl carbonate, dicresyl carbonate, dibenzyl carbonate, ethylene carbonate (1,3-dioxolan-2-one), propylene carbonate (4-methyl-1,3-dioxolan-2-one), 4-methyl-5-propyl-1,3-dioxolan-2-one, 4-phenyl-1,3-dioxolan-2-one, 4-benzyl-1,3-dioxolan-2-one, and the like. These compounds are either commercially available or can be prepared by known reactions. For example, the reaction of phosgene (COCl$_2$) with ethylene glycol yields ethylene carbonate.

Extractive Distillation Conditions

The extractive distillation of this invention can be carried out under a variety of conditions. The volume ratio of organic carbonate to feedstream will be broadly from 0.1/1 to 10/1, preferably 1/1 to 5/1. To avoid possible thermal decomposition or other reactions during the extractive distillation, head temperatures below 135° C, preferably below 100° C, are used with a reduced pressure sufficient to allow the separation to occur.

Referring to the flow diagram which further illustrates this invention, a mixture consisting essentially of phenol, cyclohexanone, and CHB is passed by 1 to an extractive distillation column 2. The organic carbonate solvent or mixture of solvents of this invention is introduced into the extractive distillation column 2 by 3 at a point above the point of introduction of the above mixture.

A vaporous overhead stream consisting essentially of cyclohexanone is withdrawn from the extractive distillation column 2. A liquid bottom stream consisting essentially of phenol, CHB, and organic carbonate is withdrawn from the extractive distillation column 2 by 4 and passed to distillation column 5.

In the distillation column 5, the phenol-CHB-organic carbonate mixture is separated into a vaporous overhead stream consisting essentially of phenol and CHB and a liquid bottom stream consisting essentially of organic carbonate which is passed by 6 and 3 to the extractive distillation column 2. Makeup organic carbonate is added by 7 if necessary. The phenol-CHB overhead stream can be passed to another separation stage to separate the mixture.

When CHB is not present in the mixture to be separated, the bottom stream from the extractive distillation column 2 will consist essentially of phenol and organic carbonate, and the overhead stream from distillation column 5 will consist essentially of phenol.

EXAMPLES

In the following examples, extractive distillations were conducted in an electrically heated 0.75" (19 mm) diameter × 35" (914 mm) length column containing 0.25" (6.4 mm) Por-Pak stainless steel perforated screen packing. The solvent was fed through a rotameter and heating section to an introduction port 3" (76 mm) from the top of the column. The mixture to be separated was fed through a rotameter and heating section to an introduction port 18" (457 mm) from the top of the column. The overhead and kettle products were collected and then analyzed by gas-liquid phase chromatography (glpc) on a Hewlett Packard 5710A chromatograph equipped with a flame ionization detector.

Fractional distillations were conducted with an electrically heated 0.75" (19 mm) diameter × 24" (610 mm) length column containing #3008 stainless steel Heli-Pak [0.092" (2.34 mm) × 0.175" (4.44 mm) × 0.175" (4.44 mm)] packing. The overhead products were collected and then analyzed by glpc.

The mixtures to be separated were prepared from commercial, reagent grade phenol and cyclohexanone and cyclohexylbenzene (98% purity) prepared by the reductive alkylation of benzene.

EXAMPLE I

An extractive distillation of a mixture containing 68 weight percent phenol, 27 weight percent cyclohexanone, and 5 weight percent CHB was conducted utilizing propylene carbonate as the solvent. The extractive distillation conditions were 120 mm Hg pressure, 84°–91° C head temperature, and 2.1/1 solvent/feed volume ratio. Over a six-hour run time, the overhead fractions contained 100 weight percent of the cyclohexanone fed to the column with an average purity of 97.9 weight percent.

A fractional distillation of the bottom fraction from the above extractive distillation, which consisted of phenol, CHB, and propylene carbonate, was conducted at 82 mm Hg pressure and head temperatures of 120°–163° C. Although earlier fractions contained as much as 9.4 weight percent propylene carbonate due to temporary overheating, the later overhead fraction contained CHB and phenol with only 1.56 weight percent propylene carbonate.

The results of this example demonstrate operability of this invention for the removal of cyclohexanone in high yield and high purity from a mixture of phenol, cyclohexanone, and CHB and for the recovery of solvent for recycle.

EXAMPLE II

In a control run, an extractive distillation of a mixture containing 68 weight percent phenol, 27 weight percent cyclohexanone, and 5 weight percent CHB was conducted with phenyl salicylate as solvent. The conditions were 80 mm Hg pressure, 85°–93° C head temperature, and a solvent/feed ratio of 3.06/1. Over a 3-hour run time, the overhead product contained 58.3 weight percent of the cyclohexanone fed to the column with a purity of 33.9 weight percent.

This extractive distillation was repeated with the same solvent, but with the pressure increased to 100 mm Hg, the head temperature increased to 99°–102° C, and the solvent/feed ratio increased to 3.2/1. Over a 4-hour run time, the overhead product contained 90.6 weight percent of the cyclohexanone fed to the column with a purity of 25.9 weight percent.

Thus, phenyl salicylate, a solvent outside the scope of this invention, does not cleanly separate cyclohexanone from the mixture of cyclohexanone, phenol, and CHB.

EXAMPLE III

In another control run, an extractive distillation of a mixture containing 70 weight percent phenol and 30 weight percent cyclohexanone was conducted with methyl oleate. The conditions were 100 mm Hg pressure, 53°–73° C head temperature, and a solvent/feed volume ratio of 4.2/1. Over a seven-hour run time, the overhead fractions contained 48.1 weight percent of the cyclohexanone fed to the column with a purity of 94.7 weight percent.

Thus, methyl oleate, a solvent outside the scope of this invention, does not cleanly remove cyclohexanone from a mixture of phenol and cyclohexanone.

Reasonable variation and modification are possible within the scope of the foregoing disclosure, the drawing, and the appended claims to the invention the essence of which is that there has been found that extractive distillation of mixtures of phenol, cyclohexanone, and cyclohexylbenzene, when it is present, to obtain cyclohexanone of high purity can be accomplished employing as solvent an organic carbonate as herein described.

I claim:

1. An extractive distillation of a mixture containing phenol and cyclohexanone, which mixture may contain cyclohexylbenzene, which comprises distilling said mixture in the presence of a solvent comprising an organic carbonate containing up to 30 carbon atoms.

2. An extractive distillation according to claim 1 wherein the solvent used in the extractive distillation of this invention contains up to 30 carbon atoms and is represented by general formula I:

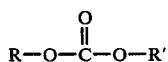

wherein R and R' are each selected from a group consisting of alkyl radicals containing 4 to 18 carbon atoms, cycloalkyl radicals containing 5 to 12 carbon atoms, aryl or substituted aryl radicals containing 6 to 12 carbon atoms with the substituent groups being one or more or a mixture of alkyl, alkoxy, cycloalkyl, halogen, or the like, and aralkyl radicals containing 7 to 12 carbon atoms, or wherein R and R' taken together form a ring represented by formula II:

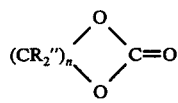

wherein $n$ is 2 or 3 and each R'' is selected from a group consisting of hydrogen, alkyl radicals, containing 1 to 4 carbon atoms, aryl or substituted aryl radicals containing 6 to 12 carbon atoms with the substituent groups being alkyl, alkoxy, cycloalkyl, halogen, or the like and aralkyl radicals containing 7 to 12 carbon atoms and the organic carbonate solvent selected has a boiling point above the boiling point of phenol (182° C at atmospheric pressure) to facilitate the separation of phenol and solvent by fractional distillation.

3. An extractive distillation of a mixture containing phenol and cyclohexanone, which mixture may contain cyclohexylbenzene, which comprises employing as a solvent an organic carbonate wherein the solvent selected is one or more of the following: dioctyl carbonate, diphenyl carbonate, dicresyl carbonate, dibenzyl carbonate, ethylene carbonate (1,3-dioxolan-2-one), propylene carbonate (4-methyl-1,3-dioxolan-2-one), 4-methyl-5-propyl-1,3-dioxolan-2-one, 4-phenyl-1,3-dioxolan-2-one, and 4-benzyl-1,3-dioxolan-2-one.

4. An extractive distillation of a mixture containing phenol and cyclohexanone, which mixture may contain cyclohexylbenzene, which comprises employing as a solvent an organic carbonate containing up to 30 carbon atoms wherein there is recovered as an overhead product high purity cyclohexanone and a kettle or bottoms stream containing the solvent, phenol, and any cyclohexylbenzene which has been present, the bottoms is subjected to fractionation to recover the solvent for reuse and a stream containing phenol and any cyclohexylbenzene which has been present.

* * * * *